United States Patent [19]

Yih et al.

[11] 4,009,021
[45] Feb. 22, 1977

[54] IMIDAZOLE PLANT GROWTH REGULATORS

[75] Inventors: Roy Y. Yih; Pyung K. Yu, both of Doylestown, Pa.

[73] Assignee: Rohm and Haas Company, Philadelphia, Pa.

[22] Filed: Oct. 30, 1975

[21] Appl. No.: 627,483

[52] U.S. Cl. .................................. 71/92; 71/89; 71/3; 260/309

[51] Int. Cl.² .............................. A01N 9/22

[58] Field of Search .................... 71/92, 86

[56] References Cited

UNITED STATES PATENTS

| | | | |
|---|---|---|---|
| 3,732,242 | 5/1973 | Buchel et al. | 260/309 |
| 3,826,836 | 7/1974 | Buchel et al. | 424/273 |
| 3,852,056 | 12/1974 | Draber et al. | 71/92 X |

FOREIGN PATENTS OR APPLICATIONS 1,935,292  1/1971  Germany ................ 71/92

*Primary Examiner*—Joseph Paul Brust
*Attorney, Agent, or Firm*—William E. Lambert, III

[57] ABSTRACT

Compounds of the formula

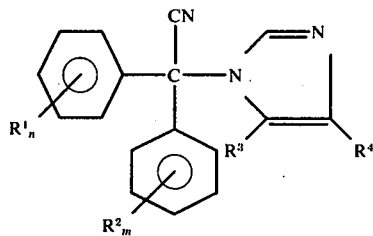

wherein
$R^1$ and $R^2$ are halogen, alkyl, alkoxy, trifluoromethyl or nitro,
$R^3$ and $R^4$ are hydrogen or alkyl, and
$n$ and $m$ are 0, 1, or 2, are useful in regulating the growth of plants when applied to the plant, plant habitat, or plant seeds.

11 Claims, No Drawings

IMIDAZOLE PLANT GROWTH REGULATORS

THE DISCLOSURE

This invention relates to the use of certain imidazoles as plant growth regulators.

In the growth cycle of many agronomic and ornamental plant species, certain undesirable or unwanted growth patterns take place. For example, in many ornamental species, compact shape or limited growth is desirable. In some crop species, undesirable secondary growth occurs. In addition, it is often advantageous to induce increased flowering or improved fruiting in other species. Consequently, various chemical compounds have been developed which function as growth regulators in attaining some of these objectives. However, the commercially available chemical growth regulators are deficient in one or more respects, such as in causing undue phytotoxicity, in inducing undesirable side effects, or in lacking either a broad spectrum of utility or utility in specific agronomic species. It has now been found that certain imidazoles have valuable activity in regulating the growth and development of plants.

The compounds useful in the present invention have the formula

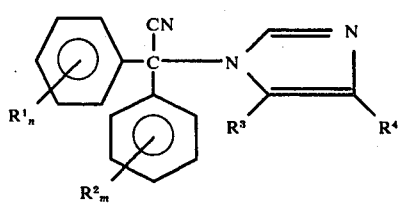

wherein
- $R^1$ is a halogen atom, preferably a chlorine or bromine atom, an alkyl group, preferably having 1 to 4 carbon atoms, an alkoxy group, preferably having 1 to 4 carbon atoms, a trifluoromethyl group, or a nitro group,
- $R^2$ is a halogen atom, preferably a chlorine or bromine atom, an alkyl group, preferably having 1 to 4 carbon atoms, an alkoxy group, preferably having 1 to 4 carbon atoms, a trifluoromethyl group, or a nitro group,
- $R^3$ is a hydrogen atom or an alkyl group, preferably having 1 to 4 carbon atoms, most preferably a methyl group,
- $R^4$ is a hydrogen atom or an alkyl group, preferably having 1 to 4 carbon atoms, most preferably a methyl group,
- $n$ is 0, 1, or 2, and
- $m$ is 0, 1, or 2, and the agronomically-acceptable acid addition salts thereof.

Among the imidazole acid addition salts which are useful in the present invention are salts with hydrochloric acid, hydrobromic acid, hydrofluoric acid, nitric acid, perchloric acid, sulfuric acid, phosphoric acid, chloroacetic acid, oxalic acid, formic acid, acetic acid, maleic acid, succinic acid, benzenesulfonic acid, p-toluenesulfonic acid, tartaric acid, lactic acid, and the like.

Typical compounds useful in the present invention include:

α,α-diphenyl-1H-imidazole-1-acetonitrile
α,α-diphenyl-1H-(4-methylimidazole)-1-acetonitrile
α,α-diphenyl-1H-(5-methylimidazole)-1-acetonitrile
α,α-diphenyl-1H-(4,5-dimethylimidazole)-1-acetonitrile
α-(4-chlorophenyl)-α-phenyl-1H--imidazole-1-acetonitrile
α-(3-methylphenyl)-α-phenyl-1H-imidazole-1-acetonitrile
α-(4-chlorophenyl)-α-phenyl-1H-(4-chloroimidazole)-1-acetonitrile
α-(4-methoxyphenyl)-α-phenyl-1H-imidazole-1-acetonitrile
α-(3-methylphenyl)-α-(2-nitrophenyl)-1H-imidazole-1-acetonitrile
α-(2,4-dichlorophenyl)-α-phenyl-1H-imidazole-1-acetonitrile
α-(4-trifluoromethylphenyl)-α-phenyl-1H-imidazole-1-acetonitrile
α-(3-butylphenyl)-α-(4-chlorophenyl)-1H-imidazole-1-acetonitrile
α,α-di(4-bromophenyl)-1H-imidazole-1-acetonitrile,
and the like.

The compounds useful in the invention can be prepared by several preparative routes. In one useful procedure, an α-phenyl-acetonitrile of the formula

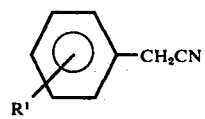

wherein $R^1$ is as defined above, is halogenated to yield the corresponding α-halo-α-phenylacetonitrile. The halogenation reaction is carried out at a temperature of about 50° to about 150° C, preferably about 100° to about 110° C, using an equimolar or excess amount of a halogenating agent such as bromine, chlorine, thionyl bromide, thionyl chloride, N-bromosuccinimide, N-chlorosuccinimide, phosphorus tribromide, phosphorus trichloride, phosphorus pentabromide, phosphorus pentachloride, or the like. Although no solvent is necessary, an inert solvent such as ethylene dichloride, carbon tetrachloride, perchloroethylene, or the like can be used. The α-halo-α-phenylacetonitrile is then reacted with benzene or a substituted benzene of the formula

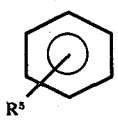

wherein $R^5$ is a halogen atom, an alkyl group, or an alkoxy group, by a Friedel-Crafts alkylation to provide a compound of the formula

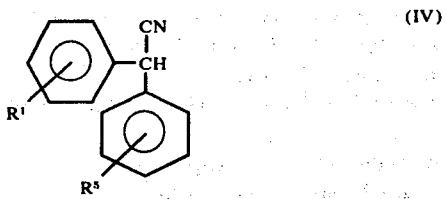

wherein $R^1$ and $R^5$ are as defined above. The Friedel-Crafts alkylation is carried out at a temperature of about −20° to about 100° C, using a Lewis acid, such as aluminum chloride, aluminum bromide, ferric chloride, titanium trichloride, stannic chloride, zinc chloride, or the like. Generally, benzene or the substituted benzene starting material is used as a solvent, but an additional inert solvent such as nitrobenzene, nitromethane, or carbon disulfide can also be used. Diphenylacetonitriles of Formula IV, and those in which $R^5$ is a trifluoromethyl group or a nitro group, can also be conveniently prepared by treating the corresponding diphenylacetamide with a suitable dehydrating agent such as phosphorus oxychloride. The compound of Formula IV is then halogenated, using the same halogenation conditions described above, and the resulting α-halo-diphenylacetonitrile is reacted with an imidazole of the formula

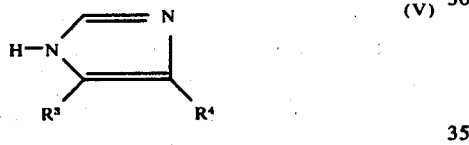

wherein $R^3$ and $R^4$ are as described above, to produce the desired compound of Formula I. Preferably greater than two equivalents of the imidazole of Formula V are used, and the reaction is carried out at a temperature of about 0° to about 200° C, and preferably about 120° to about 140° C. No solvent is necessary, but an inert solvent such as dimethylformamide, sulfolane, dimethylsulfoxide, glyme, carbon tetrachloride, toluene, benzene, or the like can be used.

The following examples will further illustrate this invention but are not intended to limit it in any way. Examples 1 to 3 show the prepartion of representative compounds useful in the invention. All temperatures are in degrees centigrade and parts and percentages by weight, unless otherwise indicated.

EXAMPLE 1

Preparation of α,α-Diphenyl-1H-imidazole-1-acetonitrile

A mixture of 25 g (0.13 m) of diphenylacetonitrile and 27 g (0.13 m) of phosphorus pentachloride is heated at 125° for 4 hours. The reaction mixture is poured into water and extracted with ether. The combined ether extracts are washed with 10% hydrochloric acid, saturated aqueous sodium bicarbonate solution and dried over magnesium sulfate. The solvent is evaporated to give 27 g of crude α-chlorodiphenylacetonitrile.

A mixture containing 27 g of α-chlorodiphenylacetonitrile and 20 g of imidazole is heated at 130° with stirring overnight. The reaction mixture is poured into water and extracted with ether. The combined ether extracts are washed with water, saturated aqueous sodium chloride solution, and dried over magnesium sulfate. The solvent is evaporated to give 16 g of a brown solid. This solid is further purified by converting to its nitrate salt and back neutralizing to the free base. A total of 12.8 g of pure α,α-diphenyl-1H-imidazole-1-acetonitrile is obtained, mp 95°–98°.

EXAMPLE 2

Preparation of α-(4-Chlorophenyl)-α-phenyl-1H-imidazole-1-acetonitrile

The title compound is prepared in a four step sequence. Bromination of p-chlorobenzyl cyanide is accomplished by slowly adding bromine to the nitrile at 105°–110°. The resultant α-bromo-4-chlorobenzyl cyanide is added without isolation to anhydrous benzene containing 1.0 equivalent of aluminum chloride (Friedel-Crafts alkylation) at reflux to afford α-phenyl-4-chlorobenzyl cyanide, mp 72°–74°. Chlorination is accomplished by exposure to phosphorus pentachloride at 110° for 16 hours to afford α-chloro-α-phenyl-4-chlorobenzyl cyanide as an oil, which is used in the step without further purification.

A mixture containing 59.0 g (0.225 mole) of α-chloro-α-phenyl-4-chlorobenzyl cyanide and 45.9 g (0.672 mole) of imidazole is heated at 130° for 3 hours, at which time it is poured into 300 ml of a 10% ammonium hydroxide solution extracted with ether. The combined organic layers are washed with water and dried. The product is purified by way of the nitrate salt. Regeneration of the free base provides 35.0 g of a viscous brown oil. Anal. Calcd. for $C_{17}H_{12}ClN_3$. C, 69.51; H, 4.12; Cl, 12.07; N, 14.30. Found: C, 69.75; H, 4.31; Cl, 11.81; N, 13.07.

EXAMPLE 3

Preparation of α,α-Diphenyl-1H-(4-methylimidazole)-1-acetonitrile and α,α-Diphenyl-1H-(5-methylimidazole)-1-acetonitrile Following the procedure of Example 1, three equivalents of methylimidazole (tautomeric mixture of 4-methyl and 5-methylimidazole) are reacted with one equivalent of α-chlorodiphenylacetonitrile. A mixture of α,α-diphenyl-1H-(4-methylimidazole)-1-acetonitrile and α,α-diphenyl-1H-(5-methylimidazole)-1-acetonitrile is obtained.

The compounds of the invention are useful for regulating plant growth. Typical plant responses include inhibition of vegetative growth in woody and herbaceous plants, control of flowering, control of fruiting, inhibition of seed formation, and related growth regulatory responses. The growth regulatory action of the compounds of the present invention may be advantageously employed in various ways. The production of shorter and thicker stems in cereal grains may reduce the tendency toward lodging. Turf grasses may be maintained at a low height and the necessity for frequent mowing alleviated. The plant growth on embankments, such as roadsides, may be controlled to prevent erosion and at the same time maintain its aesthetic value. A dormant period may be produced in certain plants. The control of flowering and fruiting may be advantageous in the production of seedless fruit and for hybridization. Delaying the vegetative process or altering the time of flowering and fruiting may result in more advantageous harvest dates or increased flower, fruit, or seed production. Useful chemical pruning of trees, shrubs, ornamentals and nursery stock may be obtained. Other applications of the compounds of the present invention will suggest themselves to those skilled in the art of agriculture.

When used as plant growth regulators, the compounds of the invention are applied to the plant, plant seeds, or plant habitat in any amount which will be sufficient to effect the desired plant response without causing a significant undesirable plant growth regulatory or phytotoxic response. Generally, the compounds of the invention will be applied to the plant or the plant habitat at a rate of about 0.1 to about 25 pounds per acre, and preferably about 0.5 to about 5 pounds per acre. When used as seed treatment agents, the compounds will usually be applied at a rate of about 0.25 to about 16 ounces per 100 pounds of seed, and preferably about 1 to about 4 ounces per 100 pounds of seed.

The compounds of the invention can be used as plant growth regulators either individually or in mixture. For example, they can be used in combination with other plant growth regulators, such as auxins, gibberellins, ethylene-releasing agents such as ethephon, pyridones, cytokinins, maleic hydrazide, succinic acid 2,2-dimethylhydrazide, choline and its salts, (2-chloroethyl) trimethylammonium chloride, triiodobenzoic acid, tributyl-2,4-dichlorobenzylphosphonium chloride, polymeric N-vinyl-2-oxazolidinones, tri(dimethylaminoethyl) phosphate and its salts, and N-dimethylamino-1,2,3,6-tetrahydrophthalamic acid and its salts, and the like, and under some conditions may be used advantageously with other agricultural chemicals such as herbicides, fungicides, insecticides, and plant bactericides.

A compound of the invention can be applied to the growth medium or to plants to be treated either by itself or, as is generally done, as a component in a growth regulant composition or formulation which also comprises an agronomically acceptable carrier. By "agronomically acceptable carrier" is meant any substance which can be used to dissolve, disperse, or diffuse a compound in the composition without impairing the effectiveness of the compound and which by itself has no detrimental effect on the soil, equipment, crops, or agronomic environment. Mixtures of the compounds of the invention may also be used in any of these formulations. The compositions of the invention can be either solid or liquid formulations or solutions. For example, the compounds can be formulated as wettable powders, emulsifiable concentrates, dusts, granular formulations, aerosols, or flowable emulsion concentrates. In such formulations, aerosols, or flowable emulsion concentrates. In such formulations, the compounds are extended with a liquid or solid carrier and, when desired, suitable surfactants are incorporated.

It is usually desirable, particularly in foliar applications, to include adjuvants, such as wetting agents, spreading agents, dispersing agents, stickers, adhesives, and the like, in accordance with agricultural practices. Examples of adjuvants which are commonly used in the art can be found in the John W. McCutcheon, Inc. publication "Detergents and Emulsifiers Annual."

The compounds of the invention can be dissolved in any appropriate solvent. Examples of solvents which are useful in the practice of this invention include water, alcohols, ketones, aromatic hydrocarbons, halogenated hydrocarbons, dimethylformamide, dioxane, dimethyl sulfoxide, and the like. Mixtures of these solvents can also be used. The concentration of the solution can vary from about 2% to about 98% with a preferred range being about 20% to about 75%.

For the preparation of emulsifiable concentrates, the compound can be dissolved in organic solvents, such as benzene, toluene, xylene, methylated naphthalene, corn oil, pine oil, o-dichlorobenzene, isophorone, cyclohexanone, methyl oleate, and the like, or in mixtures of these solvents, together with an emulsifying agent which permits dispersion in water. Suitable emulsifiers include, for example, the ethylene oxide derivatives of alkylphenols or long-chain alcohols, mercaptans, carboxylic acids, and reactive amines and partially esterified polyhydric alcohols. Solvent-soluble sulfates or sulfonates, such as alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are formulated similarly to the emulsifiable concentrates and include, in addition to the above components, water and a stabilizing agent such as a water-soluble cellulose derivative or a water-soluble salt of a polyacrylic acid. The concentration of the active ingredient in emulsifiable concentrates of usually about 10% to 60% and in flowable emulsion concentrates, this can be as high as about 75%.

Wettable powders suitable for spraying, can be prepared by admixing the compound with a finely divided solid, such as clays, inorganic silicates and carbonates, and silicas and incorporating wetting agents, sticking agents, and/or dispersing agents in such mixtures. The concentration of active ingredients in such formulations is usually in the range of about 20% to 98%, preferably about 40% to 75%. A dispersing agent may generally constitute about 0.5% to about 3% of the composition, and a wetting agent may generally consitute from about 0.1% to about 5% of the composition.

Dusts can be prepared by mixing the compounds of the invention with finely divided inert solids which may be organic or inorganic in nature. Materials useful for this purpose include, for example, botanical flours, silicas, silicates, carbonates and clays. One convenient method of preparing a dust is to dilute a wettable powder with a finely divided carrier. Dust concentrates containing about 20% to 80% of the active ingredient are commonly made and are subsequently diluted to about 1% to 10% use concentration.

Granular formulations can be prepared by impregnating s solid such as granular fuller's earth, vermiculite, ground corn cobs, seed hulls, including bran or other grain hulls, or similar material. A solution of one or more of the compounds in a volatile organic solvent can be sprayed or mixed with the granular solid and the solvent then removed by evaporation. The granular material can have any suitable size, with a preferable size range of 16 to 60 mesh. The active compound will usually comprise about 2 to 15% of the granular formulation.

The compounds of the invention can be applied as sprays by methods commonly employed, such as conventional hydraulic sprays, aerial sprays, and dusts. For low-volume applications a solution of the compound is usually used. The dilution and volume of application will usually depend upon such factors as the type of equipment employed, the method of application, and the area to be treated.

The following examples show typical applications of the compounds of the invention as plant growth regulating agents.

EXAMPLE 4

Growth Retardation of Woody Species

This example shows the application of compounds of the invention to inhibit the growth of woody plants. The following procedure is employed. Previously stratified grape seeds are washed and then sown on sand in plastic trays. The trays are kept in a propagation room until germinating plants reach 2–3 cm high. The growing young plants are transplanted into 3 inch pots. After approximately 4 to 5 weeks, the growing plants are ready for treatment. Apple seedlings included in these tests are obtained in a similar way as described for the grape seedlings.

Prior to treatment, the height of individual plants is measured and recorded. The test compound is applied at rates of 1 and 4 pounds per acre by a conventional belt sprayer at a volume of 50 gallons per acre. All of the test compounds are dissolved in an acetone/water (85:15) for application. Table I summarizes typical results obtained from these tests. Each test represents the average of several replicates.

TABLE I

Growth Retardation of Woody Species

| Compound of Example No. | Rate (lb/A) | Grape (% Inhibition) | Apple (% Inhibition) |
|---|---|---|---|
| 1 | 1 | 83 | 83 |
| 1 | 4 | 92 | 89 |
| 2 | 1 | 86 | 88 |
| 2 | 4 | 94 | 93 |
| 3 | 1 | 100 | 86 |
| 3 | 4 | 94 | 83 |

Among the other woody plants which have shown growth inhibition by the application of compound of the invention are silver maple, grapefruit, mimosa, and rhododendron.

EXAMPLE 5

Chemical Topping and Desuckering of Tobacco Plants

This example shows the application of compounds of the invention to effect chemical topping — inhibition of flower stalk formation and growth — and to control sucker growth in tobacco plants.

To evaluate chemical topping, the following procedure is employed. Seeds of a day-length neutral, Xanthi-nc variety of tobacco are lightly scattered over a mixture of loam soil and coarse sand in a tray, and covered with a thin layer of sterlizied soil. When the germinating seedlings have reached a few cm high, they are transplanted into 4 inch pots. When the plants are in early button stage, they are treated with compound of Example 1, applied in acetone/water (85:15) solution at rates of 150, 300, and 600 mg per plant by direct spray over the center of the plants. While the untreated control of plants develop blossoming flower stalks, the treated plants from neither flower stalks nor flowers.

To evaluate desuckering activity, the following procedure is employed. Tobacco seedlings propagated in a propagation room are transplanted into 6 inch pots, and the growing plants are topped at button to early flowering stage. The test solution is sprayed in a coarse spray at 20 psi, so that the solutions run down along the stalk and come in contact with axillary buds. Four weeks after treatment, the efficacy of the test compounds is determined by comparing the number of suckers, sucker weight and phytotoxicity of treated plants with that of the untreated controls. The compound of Example 1 is applied to a commercial flue-cured tobacco variety at a rate of 150 mg per plant, and to a day-length neutral Xanthi-nc tobacco hybrid at rates of 50 and 150 mg per plant. While the untreated control plants develop significant sucker growth, the treated plants evidenced no sucker growth and showed no phytotoxic response to the test compound.

EXAMPLE 6

Inhibition of Vegetative Growth of Cotton and Soybean Plants

This example shows the application of compounds of the invention to inhibit new vegetative growth and provide height reduction in crops such as cotton and soybeans. Such growth inhibition may produce more compact plants, shorten their growing season, or, in soybeans, induce pod set.

The following procedure is employed in evaluating vegetative growth inhibition. Cotton seeds are planted in 4 inch pots. When the growing plants are in the 3–4 true leaf stage, they are ready for treatment. All existing leaves are marked in an India ink prior to treatment to differentiate them from potential new leaves. The compound of Example 1 is evaluated at the rates of 0.5, 2 and 4 pounds per acre. Criteria for the inhibitory activity is determined four weeks after treatment by the presence or absence of newly developed leaves. Four to five soybean seeds are planted in a 6 inch pot. Shortly after seedlings appear above the surface of the soil, all but the two most desirable seedlings are removed. When the growing plants reach the 7 to 8 trifoliate leaf stage, they are treated with the compound of Example 1 at rates of 0.5, 1, 2, and 4 pounds per acre. The growth regulatory activity is determined four weeks after treatment by comparing the heights of the treated soybean plants with those of the untreated plants. Tables II and III summarize the results of these tests.

Table II

Control of Vegetative Growth of Cotton Plants

| Rate (lbs./A) | Percent of New Vegetative[2] Growth Inhibition | Phytotoxicity[3] |
|---|---|---|
| 0.5 | 0 | 0 |
| 2 | 100 | 0 |
| 4 | 100 | 0 |
| 0 (control) | 0[1] | 0 |

[1]The untreated controls have induced an average of 2 new true leaves during the testing period.
[2]An average of 4 plants.
[3]Phytotoxicity: "0" = no injury, "10" = complete kill.

Table III

Control of Vegetative Growth of Soybean Plants

| Rate (lbs./A) | Percent Inhibition[1] | Phytotoxicity[2] |
|---|---|---|
| 0.5 | 27 | 0 |
| 1 | 26 | 0 |
| 3 | 39 | 0 |
| 4 | 49 | 1 |
| 0 (control) | 0 | 0 |

[1]An average of 4 replicates.
[2]Phytotoxicity: "0" = no injury, "10" = complete kill.

We claim:

1. A method for regulating plant growth which comprises applying to a plant, to plant seeds, or to the locus of a plant an effective amount of a compound of the formula

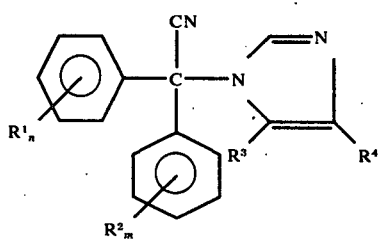

wherein
R$^1$ is a halogen atom, a (C$_1$–C$_4$)alkyl group, a (C$_1$–C$_4$)alkoxy group, a trifluoromethyl group, or a nitro group,
R$^2$ is a halogen atom, a (C$_1$–C$_4$)alkyl group, a (C$_1$–C$_4$)alkoxy group, a trifluoromethyl group, or a nitro group,
R$^3$ is a hydrogen atom or a (C$_1$–C$_4$)alkyl group,
R$^4$ is a hydrogen atom or a (C$_1$–C$_4$)alkyl group,
$n$ is 0, 1, or 2, and
$m$ is 0, 1, or 2,
or an agronomically-acceptable acid addition salt thereof.

2. The method of claim 1 wherein R$^3$ and R$^4$ are hydrogen atoms.

3. The method of claim 2 wherein $n$ and $m$ are 0.

4. The method of claim 2 wherein $n$ is 1 or 2, R$^1$ is a halogen atom, and $m$ is 0.

5. The method of claim 1 wherein $n$ and $m$ are 0, one of R$^3$ and R$^4$ is a methyl group, and one of R$^3$ and R$^4$ is a hydrogen atom.

6. The method of claim 1 wherein the compound is applied to the plant or the locus of the plant and the effective amount is about 0.1 to about 25 pounds of the compound per acre.

7. The method of claim 1 wherein the plant is woody.

8. The method of claim 1 wherein the plant is herbaceous.

9. The method of claim 1 wherein the compound is applied to plant seeds and the effective amount is about 0.25 to about 16 ounces per 100 pounds of seed.

10. The method of claim 1 wherein the plant is an agronomic crop species.

11. The method of claim 1 wherein the plant is an ornamental.

* * * * *